United States Patent
Masini (10) Patent No.: US 6,200,350 B1
(45) Date of Patent: Mar. 13, 2001

(54) ANTI-IMPINGEMENT FEMORAL PROSTHESES

(75) Inventor: Michael A. Masini, Ann Arbor, MI (US)

(73) Assignee: MedIdea, LLC, Ann Arbor, MI (US)

( * ) Notice: Subject to any disclaimer, the term of this patent is extended or adjusted under 35 U.S.C. 154(b) by 0 days.

(21) Appl. No.: 09/411,738

(22) Filed: Oct. 1, 1999

(51) Int. Cl.$^7$ .................................................. A61F 2/36
(52) U.S. Cl. .................................. 623/23.15; 623/23.35
(58) Field of Search ............................. 623/23.11, 23.15

(56) References Cited

U.S. PATENT DOCUMENTS

| | | | |
|---|---|---|---|
| 4,822,370 | 4/1989 | Schelhas | 623/23 |
| 4,938,770 | 7/1990 | Frey et al. | 623/23 |
| 4,957,510 * | 9/1990 | Cremascoli | 623/22.46 |
| 4,978,359 | 12/1990 | Wilhelm et al. | 623/23 |
| 5,387,244 | 2/1995 | Breard | 623/23 |
| 5,580,352 * | 12/1996 | Sekel | 623/22.46 |
| 5,876,459 | 3/1999 | Powell | 623/18 |

* cited by examiner

Primary Examiner—David J Isabella
(74) Attorney, Agent, or Firm—Gifford, Krass, Groh, Sprinkle, Anderson & Citkowski, PC (57) ABSTRACT

A proximal femoral prosthesis minimizes impingement, thereby affording an enhanced range of motion as compared to existing devices. The central portion of the neck of a prosthesis according to the invention is oriented distally relative to a straight line drawn between the ball portion and a point of interconnection to the exposed portion of the stem. Such a configuration reduces impingement in flexion/internal rotation and extension/external rotation, assuming an appropriately placed acetabular component. In the preferred embodiment, the neck is curved between the head and the neck. In alternative embodiments, the neck may be provided in straight and/or modular segments. The invention is compatible with neck-shaft angles, offsets, head sizes, and other dimensions commonly designated with respect to available implants.

20 Claims, 3 Drawing Sheets

ANTI-IMPINGEMENT FEMORAL PROSTHESES

FIELD OF THE INVENTION

This invention relates generally to orthopaedic surgery and, more particularly, to a proximal femoral prosthesis facilitating an enhanced range of motion.

BACKGROUND OF THE INVENTION

In total hip arthroplasty, the defective head and neck of the proximal femur are removed and replaced with a prosthetic element. Although extramedullary units are available, intramedullary prostheses are more commonly employed, which feature an elongated stem adapted for insertion and fixation within the femoral canal.

Figure 1:
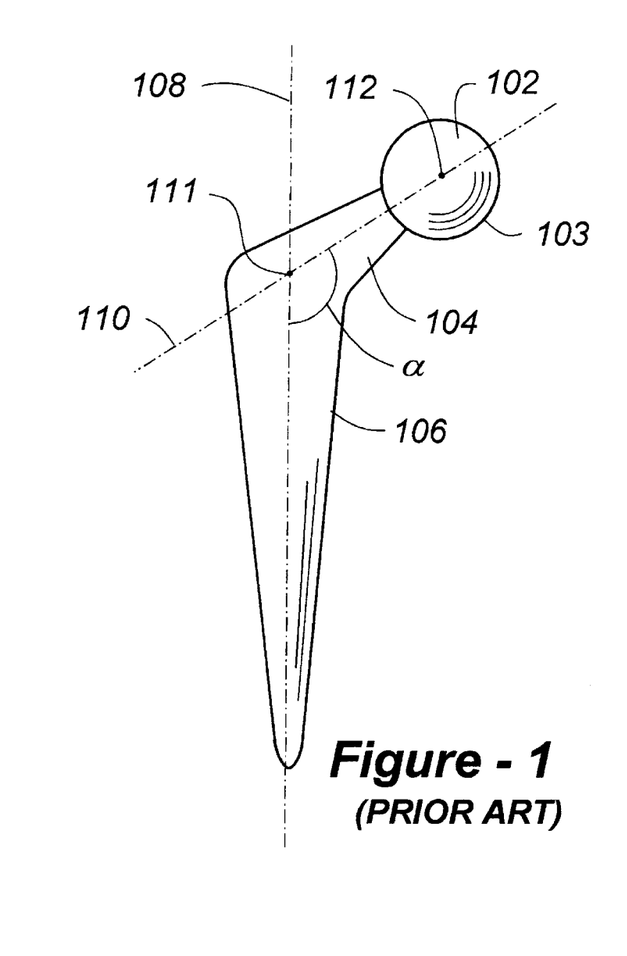
FIG. 1 is a front-view drawing of a prior-art proximal femoral endoprosthesis having a straight neck.

FIG. 1 is a generalized representation of a prior-art proximal femoral endoprosthesis. A head portion 102 having an outer surface 103 which is at least partially hemispherical is joined to a stem 106 through a neck portion 104. Such interconnections may be permanent and integral, or modular connections may be used in conjunction with tapered metal joints, for example.

The stem 106 defines a first axis 108 which is aligned more or less to the longitudinal axis of the femur, depending upon the style of the particular implant. The neck 104 defines a second axis 110 which intersects with the first axis 108 at a neck/shaft angle which may be varied in accordance with the physiology of the recipient or the desires of a given manufacturer. A typical neck/shaft angle $\alpha$ is on the order of 135°. The offset, or distance from the head portion to the axis of the stem, may also varied to achieve a desired result. A number of other variations exist, including cemented versus cementless interfaces, curved versus straight stem profiles, differently sized balls, and so forth.

In all existing configurations, the neck is straight or, in some cases, curved upwardly (or proximally) away from a plane transverse to the axis of the stem. That is to say, a centroid drawn from a central region 112 of the head 102 to a point of intersection 111 with the stem axis 108 is straight or occasionally curved to create a convex neck surface in existing designs. Such a configuration has several shortcomings. For one, as manufacturers decrease the neck-shaft angle $\alpha$ to improve offset and abductor tension, patients lose movement in flexion secondary to impingement of the neck on the acetabular component.

SUMMARY OF THE INVENTION

This invention resides in proximal femoral prostheses which minimize impingement, thereby affording an enhanced range of motion as compared to existing devices. Broadly, the central portion of the neck of the inventive prosthesis is oriented downwardly relative to a straight line drawn between the ball portion and the point of interconnection to the exposed portion of the stem. Such a configuration reduces impingement in flexion/internal rotation and extension/external rotation, assuming an appropriately placed acetabular component. In the preferred embodiment, the neck is curved between the head and the neck, though, in alternative embodiments, the neck may be provided in straight and/or modular segments. The invention is compatible with neck-shaft angles, offsets, head sizes, and other dimensions commonly designated with respect to available implants. The neck may also be curved in the transverse plane adding increased anteversion or retroversion to the neck-shaft relationship.

DETAILED DESCRIPTION OF THE INVENTION

Having discussed the prior-art design of FIG. 1 in the Background of the Invention, reference will now be made to FIG. 2, which illustrates a preferred embodiment of the invention. As with existing devices, a femoral endoprosthesis according to the invention features a stem (206), head or ball portion (202) and a neck 204. For the sake of reference, a straight line 210 has been drawn from a point 211 ("X") intersecting the axis 208 ("S") of the stem and the center 212 ("C") of the head 202. In contrast to existing devices, wherein the neck is either straight or curved upwardly or proximally relative to the straight line, the neck 204 of a prosthesis utilizing the invention curves downwardly or distally relative to the line 210.

More particularly, the centroid of the neck, which in this case is defined as the centerline 220 through the center of each cross section taken along the body of the neck is, at least the mid section (222), below or distal to the straight line 210 between the intersection 211 with the axis 208 of the of the stem and the center 212 of the ball.

Not each point of the neck according to the invention need be below or distal to the straight line 210, but rather, only a portion of the centerline. If one considers that the neck 204 includes a first portion 201 connected to the stem 206, and a second portion 203 connected to the head 202, if one draws a line tangent to the curve 220 at the point "X" and a second line tangent to the curve 210 at the point "C," they will intersect at a point "P," and it at least this point "P" which is distal to or below the straight line 210. In addition, although the neck according to the invention is said to be curved, it need not be a smooth, continuous curve as shown in FIG. 2, but rather, may be made up of one or more straight segments such as 302 and 304, as shown in FIG. 3. In this configuration, the first segment 301 includes a substantially straight longitudinal axis 302 ("$n_1$"), which intersects with the longitudinal axis ("s") of the stem 300 at an angle $a_1$. The second segment of the neck, associated with connection with a head 305, includes a second substantially straight longitudinal axis 304 ("$n_2$"), which intersects with $N_1$ at the point "p," without having to straight tangents to a curve. Note also, that in both of the embodiments of FIGS. 2 and 3, if one extends the axis of the second segment of the neck associated with interconnection to the head or ball portion, the angle formed between this line and the stem "s" ("$a_2$"), is at all times greater than the angle $A_1$ formed between the axis of the first segment associated with interconnection to the stem, and the longitudinal axis of the stem "s." This is in contrast to existing devices, wherein these two angles are either the same, or wherein $a_1$ is greater than $a_2$, indicating that the neck curves downwardly as opposed to upwardly, thereby potentially exacerbating problems with impingement.

Figure 4:
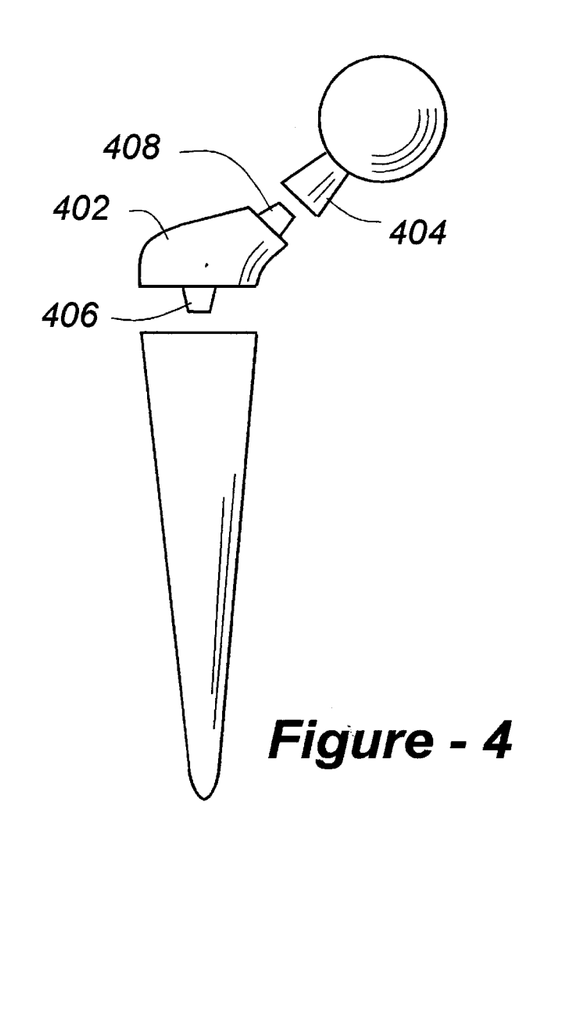
FIG. 4 is a front-view drawing of a further alternative embodiment of the invention having a modular neck.

Furthermore, a prosthesis having a neck according to the invention need not be solid and integral but instead, may utilize modular segments. FIG. 4 is representative, wherein a module 402 fits to a stem through a joint having post 406, and a head portion 404 attaches to the module 402 though a mating connector 408. Other arrangements are possible, including additional and differently configured modules, so long a least a portion of the centroid through the finally assembled structure is below or distal to a straight line from the center of the ball to a point of intersection with the axis of the stem.

Figure 5:
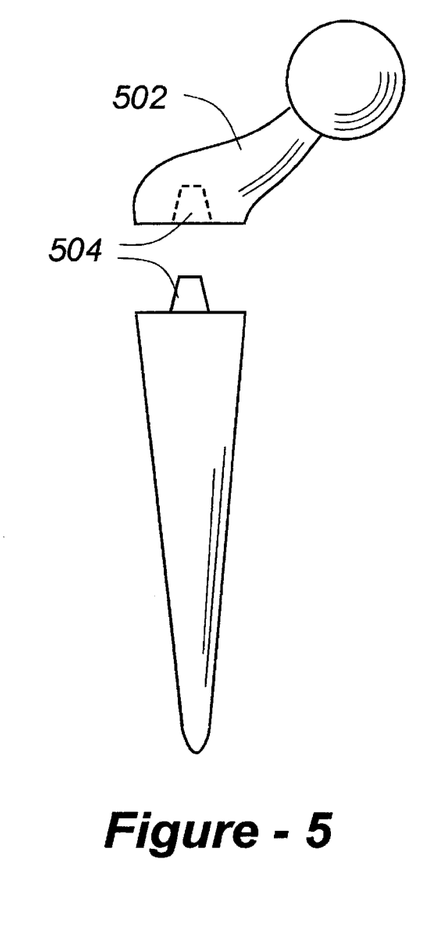
FIG. 5 is a front-view drawing of a different alternative embodiment of the invention including a modular connection between an anti-impinging neck an d implant.
Figure 6:
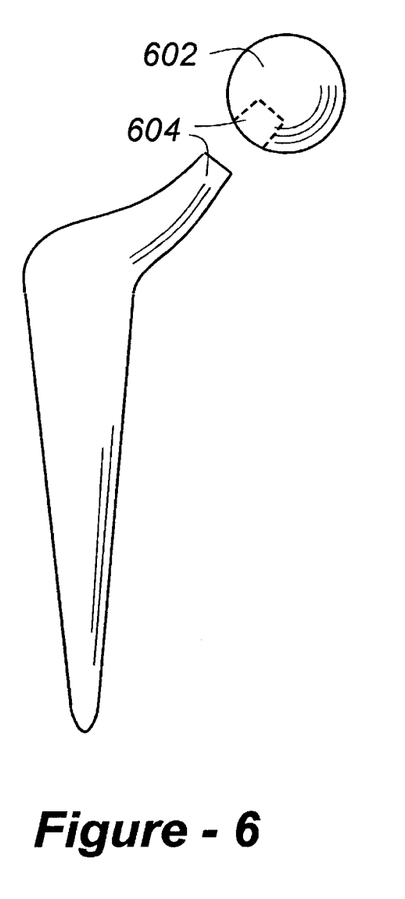
FIG. 6 illustrates yet a different embodiment, wherein a modular ball component connects to an integral neck/stem.

FIG. 5 illustrates a different alternative embodiment, wherein an anti-impinging neck component 502 is integral with a ball portion, but connects to a stem through a joint 504. FIG. 6 illustrates a different configuration, wherein the neck and stem are integral, but a modular ball 602 connects to an end of the stem through the joint 604.

Figure 2:
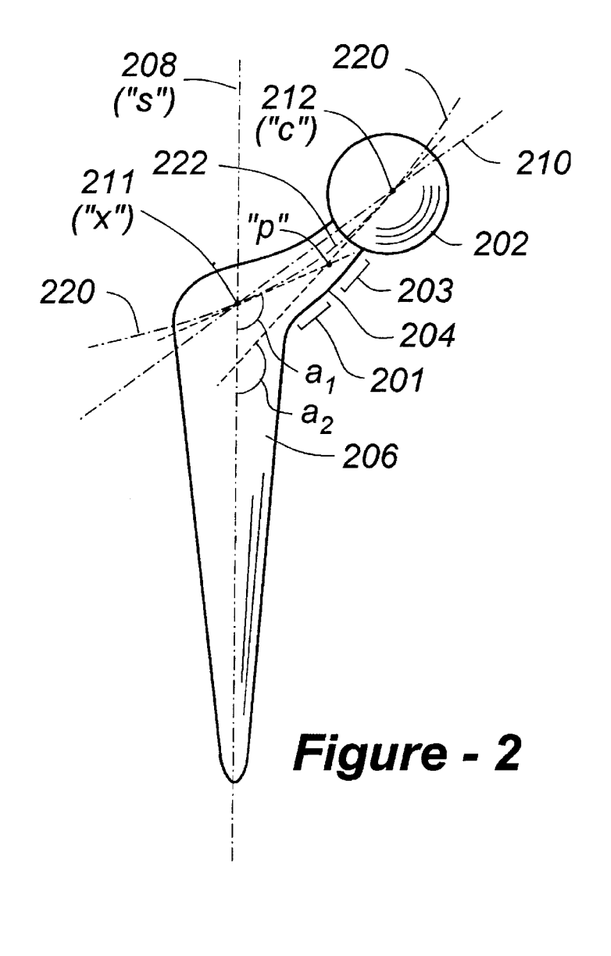
FIG. 2 is a front-view drawing of a proximal femoral endoprosthesis according to the invention having a curved neck which reduces impingement.
Figure 3:
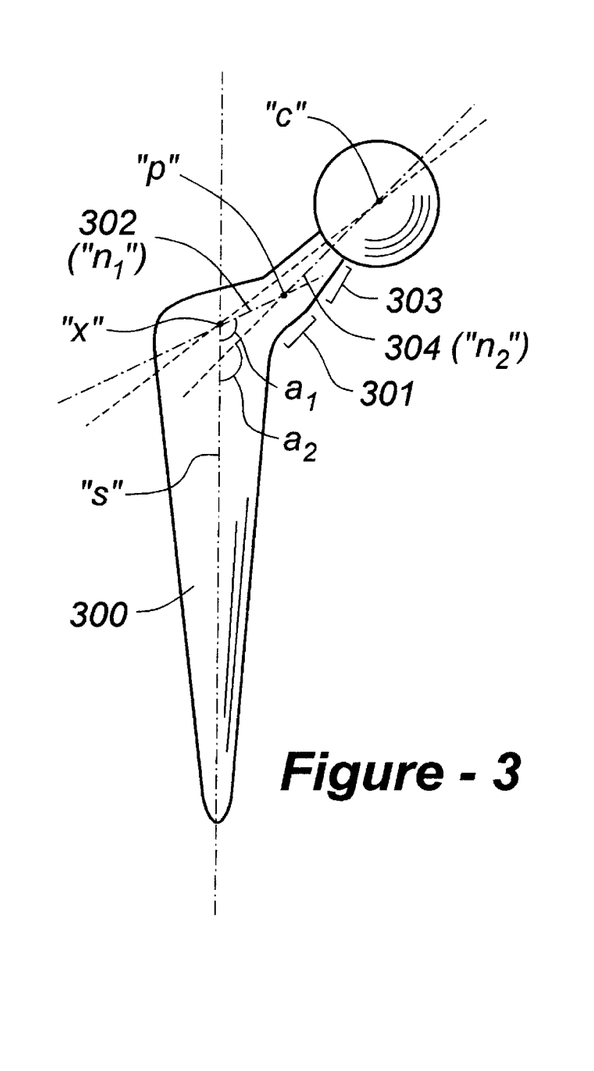
FIG. 3 is a front-view drawing of an alternative embodiment of the invention having an anti-impingement neck provided in multiple straight segments.
Figure 7A:
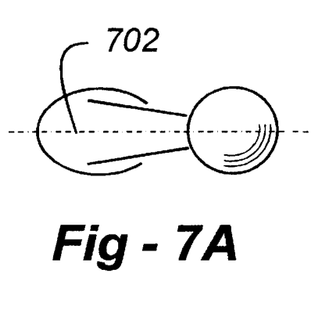
FIG. 7A is a top-view drawing illustrating how an anti-impinging neck may be curved only within the coronal plane through the head, neck and stem.
Figure 7B:
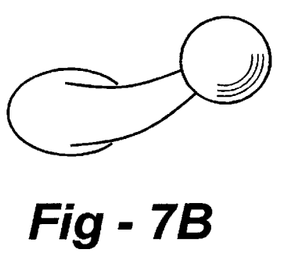
FIG. 7B illustrates how a neck according to the invention may be curved apart from, or in addition to a curve in the coronal plane so as to avoid impingement.
Figure 7C:
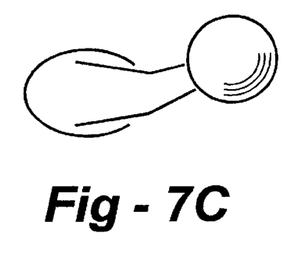
FIG. 7C illustrates how "curves" relative to the coronal plane need not be smooth and continuous, but may be piecewise.

Although a femoral prosthesis according to the invention may be curved only in the coronal plane, which may be defined as that plane which intersects the central portions of the head, neck and stem, as shown in FIG. 2, in particular, the neck according to the invention may also be curved relative to the coronal plane whether in a simple or compound configuration. Reference is made to FIG. 7A, which shows a top-down view of a femoral prosthesis which, according to the invention, would have the ball portion curve upwardly and away from the paper in a manner which is different from prior art configurations. But in addition to such an upward curve in the coronal plane 702, in the neck may also be curved relative to the coronal plane, whether or not it is also curved within the coronal plane. That is, the curve of the neck may be piecewise as opposed to continuous, as shown in FIG. 7C.

I claim:

1. An enhanced range-of-motion femoral prosthesis, comprising:

a stem having a distal portion adapted for placement within an intramedullary canal, a proximal end, and longitudinal stem axis "s";

a head configured to co-act with a corresponding acetabular component; and a neck connecting the head to the proximal end of the stem, the neck having a first segment with a longitudinal axis $n_1$ where the neck connects to the stem, and a second segment with a longitudinal axis $n_2$ where the neck connects to the head, wherein $n_1$ forms an angle $a_1$ with s, and $n_2$ forms an angle $a_2$ with s, and $a_2$ is greater than $a_1$ to reduce impingement of the neck on the acetabular component.

2. The femoral prosthesis of claim 1, wherein:

the neck is curved; and $n_1$ and $n_2$ are lines tangent to the curve where the neck connects to the stem and to the head, respectively.

3. The femoral prosthesis of claim 1, wherein $n_1$ and $n_2$ are substantially straight segments.

4. The femoral prosthesis of claim 1, wherein the neck is modularly attached to the head.

5. An enhanced range-of-motion femoral endoprosthesis, comprising:

an elongated stem component having a longitudinal axis "s" and a proximal-to-distal orientation when implanted;

a head component having a center point "c"; and a neck component connecting the head component to the stem component, the neck component having a first segment with a longitudinal axis $n_1$ that intersects with s at a point "x" and a second segment with a longitudinal axis $n_2$ that intersects with c, and wherein $n_1$ intersects $n_2$ at a point "p" distally below a straight line drawn between c and x to reduce impingement of the neck on the acetabular component.

6. The femoral endoprosthesis of claim 5, wherein:

the centerline of the neck is curved; and $n_1$ and $n_2$ are lines tangent to the curve where the neck connects to the stem and to the head, respectively.

7. The femoral endoprosthesis of claim 5, wherein at least the first and second segments are substantially straight.

8. The femoral endoprosthesis of claim 5, including a modular connection between the head and neck components or between the neck and stem components.

9. The femoral endoprosthesis of claim 5, wherein:

a coronal plane is defined as a plane which intersects s and c; and p lies outside the coronal plane.

10. A femoral endoprosthesis, comprising:

a head portion having a center;

a stem portion having an axis with an upwardly oriented proximal end when installed; and a neck portion interconnecting the head to the stem, the neck portion having a longitudinal axis which is curved or angled relative to a plane intersecting the center of the head and the axis of the stem such that at least a portion of the longitudinal axis of the neck lies outside the plane.

11. The femoral endoprosthesis of claim 10, wherein the head portion is modularly attached to the neck portion.

12. The femoral endoprosthesis of claim 10, wherein the neck portion is modularly attached to the stem portion.

13. The femoral endoprosthesis of claim 10, wherein the neck portion is also curved or angled upwardly within the plane.

14. The femoral prosthesis of claim 4, wherein the neck extends from a body modularly attached to the stem.

15. The femoral prosthesis of claim 14, wherein the body is modularly attached to the stem by means of a Morse-type taper connection.

16. The femoral prosthesis of claim 14, wherein the head is modularly attached to the body by means of a Morse-type taper connection.

17. An enhanced range-of-motion femoral prosthesis, comprising:

a stem having a distal portion adapted for placement within an intramedullary canal, a proximal end with a modular connector, and longitudinal stem axis, s;

a head configured to co-act with a corresponding acetabular component;

a body attached to the modular connector, the body including a neck portion having a first segment with a longitudinal axis $n_1$ where the neck portion connects to the body, and a second segment with a longitudinal axis $n_2$ where the neck portion connects to the head, wherein $n_1$ forms an angle $a_1$ with s, and $n_2$ forms an angle $a_2$ with s, and wherein $a_2$ is greater than $a_1$ to reduce impingement of the neck on the acetabular component.

18. The femoral prosthesis of claim 17, wherein the modular connector includes a Morse-type taper.

19. The femoral prosthesis of claim 17, wherein the head is modularly connected to the neck portion.

20. The femoral prosthesis of claim 19, wherein the head is modularly connected to the neck portion through a Morse-type taper.

* * * * *

UNITED STATES PATENT AND TRADEMARK OFFICE
CERTIFICATE OF CORRECTION

PATENT NO. : 6,200,350 B1
DATED : March 13, 2001
INVENTOR(S) : Masini

Page 1 of 1

It is certified that error appears in the above-identified patent and that said Letters Patent is hereby corrected as shown below:

On Title page, item
(56) References Cited - U.S. Patent Documents

| | | | |
|---|---|---|---|
| 4,790,852 | 12/1988 | Noiles | 623/18 |
| 4,846,839 | 7/1989 | Noiles | 623/18 |

Signed and Sealed this

Fifth Day of June, 2001

*Attest:*

*Attesting Officer*

NICHOLAS P. GODICI
*Acting Director of the United States Patent and Trademark Office*

US006200350C1

(12) EX PARTE REEXAMINATION CERTIFICATE (5127th)
United States Patent
Masini (10) Number: US 6,200,350 C1
(45) Certificate Issued: Jun. 28, 2005

(54) ANTI-IMPINGEMENT FEMORAL PROSTHESES

(75) Inventor: Michael A. Masini, Ann Arbor, MI (US)

(73) Assignee: Medidea, LLC, Ann Arbor, MI (US)

Reexamination Request:
No. 90/006,500, Dec. 30, 2002

Reexamination Certificate for:
Patent No.: 6,200,350
Issued: Mar. 13, 2001
Appl. No.: 09/411,738
Filed: Oct. 1, 1999

Certificate of Correction issued Jun. 5, 2001.

(51) Int. Cl.$^7$ .................................................. A61F 2/36
(52) U.S. Cl. .................................. 623/23.15; 623/23.35
(58) Field of Search ............................ 623/23.35, 23.15

(56) References Cited

U.S. PATENT DOCUMENTS

| | | | |
|---|---|---|---|
| 3,848,272 A | 11/1974 | Noiles | 3/1 |
| 4,279,041 A | 7/1981 | Buchholz | 3/1.912 |
| 4,822,370 A | 4/1989 | Schelhas | 623/23 |
| 4,908,035 A | 3/1990 | Deckner et al. | 623/23 |
| 4,978,356 A | 12/1990 | Noiles | 623/18 |
| 5,002,578 A | 3/1991 | Luman | 623/23 |
| 5,002,581 A | 3/1991 | Paxson et al. | 623/23 |
| 5,030,234 A | 7/1991 | Pappas et al. | 623/23 |
| 5,030,238 A | 7/1991 | Nieder et al. | 623/23 |
| 5,047,062 A | 9/1991 | Pappas et al. | 623/23 |
| 5,080,685 A | 1/1992 | Bolesky et al. | 623/23 |
| 5,108,452 A | 4/1992 | Fallin | 623/23 |
| 5,201,882 A | 4/1993 | Paxson | 623/23 |
| 5,342,363 A | 8/1994 | Richelsoph | 606/79 |
| 5,358,526 A | 10/1994 | Tornier | 623/19 |
| 5,387,244 A | 2/1995 | Breard | 623/23 |
| 5,507,818 A | 4/1996 | McLaughlin | 623/18 |
| 5,507,819 A | 4/1996 | Wolf | 623/19 |
| 5,507,830 A | 4/1996 | DeMane et al. | 623/23 |
| 5,549,682 A | 8/1996 | Roy | 623/19 |
| 5,653,764 A | 8/1997 | Murphy | 623/23 |
| 5,653,765 A | 8/1997 | McTighe et al. | 623/23 |
| 5,702,480 A | 12/1997 | Kropf et al. | 623/23 |
| 5,702,484 A | 12/1997 | Goymann et al. | 623/23 |
| 5,755,805 A | 5/1998 | Whiteside | 623/22 |
| 5,800,558 A | 9/1998 | LaHaise, Sr. | 623/23 |
| 5,876,459 A | 3/1999 | Powell | 623/18 |
| 5,888,207 A | 3/1999 | Nieder et al. | 623/23 |
| 5,902,340 A | 5/1999 | White et al. | 623/22 |
| 5,906,644 A | 5/1999 | Powell | 623/23 |
| 5,916,270 A | 6/1999 | Lipman | 623/22 |
| 6,139,583 A | 10/2000 | Johnson | 623/23 |
| 6,238,436 B1 | 5/2001 | Lob et al. | 623/22.42 |

(Continued)

FOREIGN PATENT DOCUMENTS

| | | | |
|---|---|---|---|
| EP | 0363019 A2 | 11/1990 | A61F/2/36 |
| EP | 0359672 B1 | 11/1992 | A61F/2/36 |
| EP | 0552949 B1 | 7/1993 | A61F/2/34 |

OTHER PUBLICATIONS

Zimmer Revision Taper Hip Prosthesis.
Portland Orthopaedics advertisement for Margron Hip Replacement System, Copyright 2002.

(Continued)

*Primary Examiner*—Corrine McDermott (57) ABSTRACT

A proximal femoral prosthesis minimizes impingement, thereby affording an enhanced range of motion as compared to existing devices. The central portion of the neck of a prosthesis according to the invention is oriented distally relative to a straight line drawn between the ball portion and a point of interconnection to the exposed portion of the stem. Such a configuration reduces impingement in flexion/internal rotation and extension/external rotation, assuming an appropriately placed acetabular component. In the preferred embodiment, the neck is curved between the head and the neck. In alternative embodiments, the neck may be provided in straight and/or modular segments. The invention is compatible with neck-shaft angles, offsets, head sizes, and other dimensions commonly designated with respect to available implants.

U.S. PATENT DOCUMENTS

| | | | |
|---|---|---|---|
| 6,306,174 B1 | 10/2001 | Gie et al. | 623/22.42 |
| 6,413,280 B1 | 7/2002 | Feiler | 623/22.15 |
| 6,436,147 B1 | 8/2002 | Zweymuller | 623/22.41 |
| 2002/0038148 A1 | 3/2002 | Fernandez et al. | 623/23.18 |
| 2002/0052661 A1 | 5/2002 | Spotorno et al. | 623/23.48 |
| 2002/0058999 A1 | 5/2002 | Dwyer et al. | 623/22.42 |
| 2002/0059000 A1 | 5/2002 | Dwyer et al. | 623/22.43 |
| 2002/0120343 A1 | 8/2002 | Doubler et al. | 623/22.42 |

OTHER PUBLICATIONS

Range of Motion of the Hip, The Orthopaedic Forum, vol. 82–A, No. 11, Nov. 2000.

Huo et al., Custom–Designed Femoral Prostheses in Total Hip Arthroplasty Done with Cement for Severe Dysplasia of the Hip, The Journal of Bone and Joint Surgery, vol. 75–A, No. 10, Oct. 1993.

Long–Term Results of Total Hip Arthroplasty with a Cemented Custom–Designed Swan–Neck Femoral Component for Congenital Dislocation or Severe Dysplasia, DiFazio et al., Journal of Bone and Joint Surgery, vol. 84–A, No. 2, Feb. 2002.

Zimmer Modular Revision (ZMR) Hip System.

Whiteside et al., Fixation of the Quadralock Femoral Component: A Biomechanical and Clinical Study, Clinical Orthopedics and Related Research, vol. I (393), Dec. 2001.

Krushell et al., Range of Motion in Contemporary Total Hip Arthroplasty, The Journal of Arthroplasty, vol. 6, No. 2, Jun. 1991.

Egan et al., Biomechanics of Total Hip Arthroplasty, Seminars in Arthroplasty, vol. 4, No. 4, Oct. 1993.

Herrlin et al., Range of Motion Caused by Design of the Total Hip Prosthesis, Acta Radiological 29 (1988).

Barrack et al., Instability After Major Joint Replacement, Orthopedic Clinics of North America, vol. 32, No. 4, Oct. 2001.

Prosthetic Design and Outcome in Total Hip Arthroplasty, The Journal of Bone & Joint Surgery, vol. 83–A, No. 5, May 2001.

McGrory, Effect of Femoral Offset on Range of Motion and Abductor Muscle Strength After Total Hip Arthroplasty, Journal of Bone Joint Surgery, vol. 77–B, No. 6, Nov. 1995.

Gondi et al., Impingement After Total Hip Arthroplasty Related to Prosthetic Component Selection and Range of Motion, Journal of the Southern Orthopaedic Association, vol. 6, No. 4, Winter 1997.

Barrack et al., The Effect of Component Design on Range of Motion to Impingement in Total Hip Arthroplasty, AAOS Instructional Course Lectures, vol. 50, 2001.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 5–9 is confirmed.

Claims 10–13 are cancelled.

Claims 1 and 17 are determined to be patentable as amended.

Claims 2–4, 14–16 and 18–20, dependent on an amended claim, are determined to be patentable.

1. An enhanced range-of-motion femoral prosthesis, comprising:
    a stem having a distal portion adapted for placement within an intramedullary canal, a proximal end, and longitudinal stem axis, [" ]s[" ];
    a head *having a center, c,* configured to co-act with a corresponding acetabular component; and
    a neck connecting the head to the proximal end of the stem, the neck having a first segment with a longitudinal axis $n_1$ where the neck connects to the stem, and a second segment with a longitudinal axis $n_2$ where the neck connects to the head, wherein $n_1$ forms an angle $a_1$ with s, and $n_2$ forms an angle $a_2$ with s, *where $n_1$ and $n_2$ intersect at a point, p,* and *wherein* $a_2$ is greater than $a_1$, *and the offset between c and s is greater than the offset between p and s to reduce impingement of the neck on the acetabular component.*

17. An enhanced range-of-motion femoral prosthesis, comprising:
    a stem having a distal portion adapted for placement within an intramedullary canal, a proximal end with a modular connector, and longitudinal stem axis, s;
    a head *having a center "c"* configured to co-act with a corresponding acetabular component;
    a body attached to the modular connector, the body including a neck portion having a first segment with a longitudinal axis $n_1$ where the neck portion connects to the body, and a second segment with a longitudinal axis $n_2$ where the neck portion connects to the head,
    wherein $n_1$ forms an angle $a_1$ with s, and $n_2$ forms an angle $a_2$ with s, *where $n_1$ and $n_2$ intersect at a point, p,* and wherein $a_2$ is greater than $a_1$, *and the offset between c and s is greater than the offset between p and s to reduce impingement of the neck on the acetabular component.*

* * * * *